United States Patent
Oku et al.

(10) Patent No.: US 8,343,951 B2
(45) Date of Patent: Jan. 1, 2013

(54) VOLATILE SULFIDE PRODUCTION INHIBITOR AND METHOD FOR INHIBITING THE PRODUCTION OF VOLATILE SULFIDE USING THE INHIBITOR

(75) Inventors: Kazuyuki Oku, Okayama (JP); Mayumi Kurose, Okayama (JP); Hiroto Chaen, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 638 days.

(21) Appl. No.: 12/280,470

(22) PCT Filed: Feb. 21, 2007

(86) PCT No.: PCT/JP2007/053173
§ 371 (c)(1),
(2), (4) Date: Aug. 22, 2008

(87) PCT Pub. No.: WO2007/097357
PCT Pub. Date: Aug. 30, 2007

(65) Prior Publication Data
US 2009/0018217 A1 Jan. 15, 2009

(30) Foreign Application Priority Data
Feb. 22, 2006 (JP) ................. 2006-045941

(51) Int. Cl.
*A01N 43/00* (2006.01)
*A61K 31/33* (2006.01)
*C12P 19/60* (2006.01)

(52) U.S. Cl. .......................... 514/183; 435/75
(58) Field of Classification Search .................. 514/183
See application file for complete search history.

(56) References Cited

U.S. PATENT DOCUMENTS

| | | | | |
|---|---|---|---|---|
| 4,123,426 A * | 10/1978 | Katayama et al. | ............ | 530/407 |
| 5,084,563 A | 1/1992 | Sakai et al. | | |
| 6,576,446 B2 * | 6/2003 | Yamasaki et al. | ............... | 435/74 |
| 2006/0134197 A1 | 6/2006 | Uchida et al. | | |
| 2006/0194743 A1 | 8/2006 | Oku et al. | | |

FOREIGN PATENT DOCUMENTS

| | | |
|---|---|---|
| EP | 1 541 660 | 6/2005 |
| EP | 1 582 105 | 10/2005 |
| EP | 1 588 627 | 10/2005 |
| EP | 1 600 496 | 11/2005 |
| JP | 3135992 A | 6/1991 |
| JP | 10084866 A | 4/1998 |
| JP | 2005013227 A * | 1/2005 |
| JP | 2005060237 A | 3/2005 |
| JP | 05095148 | 4/2005 |
| JP | 2005239655 A | 9/2005 |
| JP | 2006094856 A | 4/2006 |
| JP | 2006188672 A | 7/2006 |
| WO | 0210361 A1 | 2/2002 |
| WO | 2004047559 A1 | 6/2004 |
| WO | 2004060077 A1 | 7/2004 |
| WO | 2006/022174 | 3/2006 |

OTHER PUBLICATIONS

Mottram (Chemical tainting of foods.International Journal of Food Science & Technology vol. 33, Issue 1, pp. 19-29, Feb. 1998).*
Supplementary European Search Report to EP Application No. 07714673.6 dated Dec. 19, 2011 (8 pages).
KidsHealth: "Why do feet stink?," Internet archive WayBackMachine, retrieved from the Internet on Nov. 24, 2011 at http://web.archive.org/web/20051222211859/http://kidshealth.org/kid/talk/yucky/feet_stink.html, Dec. 22, 2005 (three pages).
Aga, Hajime, "Tokushu Kinosei Shokuhin no Kaihatsu ni Mukete L-Ascorbic Acid 2-Glucoside no Kinosei", Kagaku to Kogyo, 2005, vol. 79, No. 7, pp. 303-309.
Jung, M.Y. et al., "Singlet Oxygen and Ascorbic Acid Effects on Dimethyl Disulfide and Off-Flavor in Skim Milk Exposed to Light", Journal of Food Science, 1998, vol. 63, No. 3, pp. 408-412.
Kurose, Mayumi et al., "Ascorbic Acid 2-Glucoside 1 7 no Shuki Yokusei Sayo", Japanese Society for Food Science and Technology Taikai Koenshu, 2006, 53rd, p. 119.
Mitsuzumi Hitoshi, "Shinki Shitei Tenkabutsu L-Ascorbic Acid 2-Glucoside no Tokusei to Yoto", FFI Journal, 2006, vol. 211, No. 5, pp. 435-444.
Nagata, Hiromitsu et al., "Suisan Kanzume no Kan Naimen Kokuhen no Boshi", Report of Toyo Junior College of Food Technology and Toyo Institute of Food Technology, 1987, No. 17, pp. 11-18.
Takahata Hiroyuki, "San Tenka ni yoru Kyabetsu no Kanetsushu no Yokusei to Kakohin eno Oyo", Gunmaken Nogyo Shikenjo Kenkyu Hokoku, 2001, No. 7, pp. 49-56.

* cited by examiner

*Primary Examiner* — Sreeni Padmanabhan
*Assistant Examiner* — Layla Soroush
(74) *Attorney, Agent, or Firm* — Browdy and Neimark, PLLC

(57) ABSTRACT

The object of the present invention is to establish a volatile sulfide production inhibitor that can inhibit the production of volatile sulfides from a composition and to provide a method for inhibiting the production of volatile sulfides from a composition by using the inhibitor. The object are solved by providing a volatile sulfide production inhibitor comprising L-ascorbic acid 2-glucoside as an effective ingredient and a method for inhibiting the production of volatile sulfides from a composition by incorporating the volatile sulfide production inhibitor into the composition.

2 Claims, No Drawings

VOLATILE SULFIDE PRODUCTION INHIBITOR AND METHOD FOR INHIBITING THE PRODUCTION OF VOLATILE SULFIDE USING THE INHIBITOR

TECHNICAL FIELD

The present invention relates to a volatile sulfide production inhibitor comprising α-D-glucopyronosyl-(1→2)-L-ascorbic acid (hereafter abbreviated as "AA-2G"), in which glucose binds to L-ascorbic acid (hereafter abbreviated as "ascorbic acid") by α-1,2 linkage, as an effective ingredient, and a method for inhibiting the production of a volatile sulfides from a composition characterized in that the inhibitor is incorporated into the composition.

BACKGROUND ART

Although volatile substances produced in a production process or storage of compositions such as food and beverages, cosmetics, quasi drugs, pharmaceuticals and chemical engineering products bring flavors peculiar to the composition, the volatile substances may cause the flavor alteration or deterioration in some cases. As volatile sulfides among the volatile substances make uncomfortable feeling even in minute amounts, volatile sulfide is a major factor influencing on the taste of a composition. So, inhibiting the production of volatile sulfides is a very important object for a person skilled in the art. In addition, a novel method for inhibiting volatile sulfide production is required to diversified dietary life.

For attain the above object, the applicant of the present invention disclosed a method for inhibiting the production of cooked-milk odor by the use of saccharide derivatives of α,α-trehalose in Japanese Patent Kokai No. 94856/2006. The applicant of the present invention also disclosed a composition comprising AA-2G in Japanese Patent No. 2832848, and a method for inhibiting the production of foul odor occurring along with browning of a composition in Japanese Patent Kokai No. 188672/2006. However, these patent documents mentioned no concrete description that AA-2G can inhibit the production of volatile sulfide and its effective dosage.

Ascorbic acid is used for inhibiting browning or decomposition of other easily-oxidizable substances and compositions by preventing their oxidation with its strong reducing and antioxidizing power in addition to being used as Vitamin C. However, ascorbic acid may easily react with amino acids, peptides and proteins, and it is known for occasionally enhancing browning or volatile substance production along with browning. On the other hand, AA-2G, a derivative of ascorbic acid, is more stable and less oxidizable than ascorbic acid, and so it is hard to occur browning and have an effect of inhibiting foul odor production along with browning when added to a composition (for example, q.v. Japanese Patent Kokai No. 188672/2006). However, AA-2G may enhance the volatile substance production in some usage pattern. Also, since ascorbic acid and AA-2G are strong acidic substances, when added to a composition, they may influence on the original flavor of the composition by the taste of their own or of the neutralizer used to reduce the acidic taste.

Under these circumstances, it is desired the development of a novel inhibitor of the production of volatile sulfides that cause uncomfortable feeling.

DISCLOSURE OF INVENTION

An object of the present invention is to establish a volatile sulfide production inhibitor, which can inhibit the production of volatile sulfides from a composition, and to provide a method for inhibiting the production of volatile sulfides from a composition by the inhibitor.

The inventors of the present invention have been dedicated to researching on ascorbic acid derivatives to establish an inhibitor of volatile sulfide production from a composition. As a result of the research, it was found that AA-2G, which has neither reducing power nor antioxidant effect and has been thought to enhance the production of volatile substance, unexpectedly exert outstanding function of inhibiting the production of a volatile sulfide from a composition when incorporated into the composition in contrast to or more efficiently than ascorbic acid. It was found also that the effect of inhibiting the production of volatile sulfides from a composition by AA-2G is exerted at an extremely small amount within the range not to deteriorate the flavor of the composition added with AA-2G, and then the present invention was achieved. The present invention attains the above object by providing a volatile sulfide production inhibitor comprising AA-2G as an effective ingredient and a method for inhibiting volatile sulfide production from a composition by incorporating the inhibitor into the composition.

In accordance with the present invention, a composition in which the quality and flavor are preserved, such as foods and drinks, cosmetics, quasi drugs, pharmaceuticals, feedstuffs and baits and pet foods, can be produced by inhibiting volatile sulfide production during the manufacturing process or storage. As AA-2G is decomposed to ascorbic acid and glucose by α-glucosidase in vivo when administered into a living body orally, parenterally, by percutaneous application or injection, the composition comprising AA-2G is a volatile sulfide production inhibitor that is excellent in safety.

BEST MODE FOR CARRYING OUT THE INVENTION

A composition as referred to as in the present invention means a composition comprising sulfur amino acids or peptides containing sulfur amino acid in a liquid, semisolid or solid form, which may produce volatile sulfides by heating or long time storage. They are, for example, foods and drinks, cosmetics, quasi drugs, pharmaceuticals, feedstuff and baits, pet foods, groceries and commodities, which are orally or parenterally ingested or percutaneously applied to human or animals or applied directly on the skin, including substances parenterally administered by injection.

A volatile sulfide as referred to as in the present invention means a volatile sulfide produced in process of production or storage of a composition, which causes deterioration of flavor or quality of the composition or is included in bad breath or body odor, such as hydrogen sulfide, methyl-mercaptan, dimethyl-sulfide, dimethyl-disulfide. The volatile sulfide production inhibitor of the present invention is efficient particularly in inhibiting production of hydrogen sulfide, methyl-mercaptan and/or dimethyl-disulfide.

A volatile sulfide production inhibitor as referred to as in the present invention includes AA-2G in such amount that the volatile sulfide production from a composition is inhibited when incorporated into the composition. AA-2G in a single-agent form is acceptable as the inhibitor, and if necessary, the inhibitor can further contain one or more pharmaceutically acceptable additives for purposes of giving dispersibility, diluting, filling, or stabilizing. The amount of AA-2G incorporated into the volatile sulfide production inhibitor is from 0.1% to 100% by weight (hereinafter, "% by weight" is referred to as "%" throughout the specification unless specified otherwise), preferably from 1% to 100%, more preferably from 5% to 100%.

For a pharmaceutically acceptable additive added in the volatile sulfide production inhibitor as referred to as in the present invention, additives for foods and drinks, cosmetics, quasi drugs, pharmaceuticals and groceries can be used. Concretely, one or more following substances can be used: reducing saccharides such as glucose and maltose, α,α-trehalose, saccharide derivatives of α,α-trehalose such as α-glucosyl α,α-trehalose and α-maltosyl α,α-trehalose, non-reducing saccharides as cyclic tetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} described in International Patent Publication Wo 02/10361, cyclic tetrasaccharide having a structure of cyclo{→6)-α-D-glucopyranosyl-(1→4)-α-D-glucopyranosyl-(1→6)-α-D-glucopyranosyl-(1→4)-α-D-glucopyranosyl-(1→} described in Japanese Patent Kokai No. 95148/05 and cyclodextrins, sugar alcohols such as xylitol and maltitol, high intensity sweeteners, water soluble polysaccharides such as gums and mucopolysaccharides, inorganic acids, organic acids, salts, emulsifiers, vitamin E, erythorbic acid, catechins, chlorogenic acid, flavonoids and their derivatives, amino acids including carnitine, adenosine and its phosphates, α-lipoic acid, coenzyme Q10 (CoQ10). When one or more substances such as non-reducing saccharides, sugar alcohols, vitamin E, catechins, flavonoids and their derivatives, organic acids including lactic acid, acetic acid and citric acid, inorganic salts are used in combination with AA-2G, the effect of inhibiting volatile sulfide production can be enhanced. Particularly, use of α,α-trehalose, maltitol, saccharide derivatives of α,α-trehalose and cyclic tetrasaccharides in combination with AA-2G is preferable as they have strong effect of inhibiting volatile sulfide production.

AA-2G used in a volatile sulfides production inhibitor of the present invention is not restricted by its origin or production method. Any one of AA-2G produced by fermentation method, enzymatic method, or organic synthesis method, or purchased from the marketplace can be used. For example, as described in the specification of Japanese Patent Application No. 2005-351866, a composition produced by glycosylation of ascorbic acid by allowing an α-glycosyl transferring enzyme such as cyclomaltodextrin glucanotransferase to act on a mixture solution of ascorbic acid and starchy material such as dextrin, its partially purified one, or further purified one by removing coexisting ascorbic acid and dextrin with ion-exchange resin, resulting in elevated purity of ascorbic acid 2-glycosides including AA-2G, in which ascorbic acid binds to equal or more moles of glucose. A composition with higher purity of AA-2G produced by allowing glucoamylase to act on the above composition containing ascorbic acid 2-glycosides including AA-2G to eliminate the glucose from ascorbic acid 2-glycoside in which two or more of glucoses bind to ascorbic acid, and purifying is more preferably used because of lower contents of substances causing browning or foul odor produced from their decomposed matter. AA-2G used in a volatile sulfide production inhibitor of the present invention comprises AA-2G at a concentration of preferably 90%, more preferably 95%, much more preferably 97% or more, on a dry solid basis. When used in cosmetics, quasi drugs, or pharmaceuticals, which contain large amount of an affective ingredient such as vitamins having highly-reactivity with ascorbic acid, or used in foods and drinks containing substances such as amino acids or proteins easily causing Maillard reaction, the purity of AA-2G is preferable to be 98%.

The amount of the volatile sulfides production inhibitor of the present invention incorporated into a composition is not restricted as long as it can exert effects of inhibiting volatile sulfide production without causing large influences on texture, taste, and flavor of the composition. The additive amount of AA-2G to the whole weight of the composition is normally about 0.0005 to 0.5%, preferably about 0.001 to 0.1%, and more preferably about 0.005 to 0.1%. When the amount is lower than 0.0005%, effect of inhibiting volatile sulfides production is not exerted. When the amount is higher than 0.5%, volatile sulfides production may be enhanced or the taste of the composition may be affected. For purpose of inhibiting production of dimethyl-sulfide or dimethyl-disulfide, when the composition has acidic taste, AA-2G can be added at 0.5% or more to the whole weight of the composition as long as it has no influence on its taste or for acidulating it.

Form of the volatile sulfides production inhibitor of the present invention is not restricted. For example, any form such as syrup, massecuite, paste, powder, solid, granule, and tablet is acceptable, and can be further admixed with filler, vehicle, or binder to make into granule, globule, short rod, plate, cube, or tablet.

The volatile sulfides production inhibitor of the present invention can be incorporated into a composition in process of production, or into the end product. Concretely, combination of one or more methods such as mixing, kneading, dissolving, melting, dispersing, suspending, emulsifying, permeating, crystallizing, disseminating, applying, adhering, spray, coating, injecting, immersing, solidifying, or invert-micelling can be used.

The method for inhibiting volatile sulfides production in the present invention can be advantageously used in producing high-quality compositions, in which volatile sulfide production is inhibited, including foods and drinks such as seasonings, sweeteners, Japanese confectioneries, western confectioneries, breads, snack foods, agricultural products, stock farm products, fishery products, their processed products, their frozen products, refrigerated products, chilled products, retort products, dried products, freeze-dried products, microwave foods, cold beverages and alcohol drinks. The method of the present invention can be advantageously used also in producing high-quality compositions, in which volatile sulfides production is inhibited, including feedstuff and baits, pet foods, articles of taste, cosmetics for basic skin care or makeup, quasi-drugs, pharmaceuticals for tablet, liquid, ointment, nutritional supplement, fluid, dialysis solution, perfuse solution, and organ preserving solution. Furthermore, the method of the present invention can be used in cosmetics for oral care, body care, skin care or hair care, or deodorant to inhibit volatile sulfide production in mouth, body surface or digestive tract of animals or human, excretory substances of animals or constructions.

The present invention is explained in detail in the experiments described as follows.

Experiment 1

Effect of AA-2G on Hydrogen Sulfide Production

The experiments to investigate the effect of AA-2G on hydrogen sulfide production were carried out as follows.

Preparation of Samples for Measurement of Hydrogen Sulfide Production

AA-2G (reagent grade, commercialized by Hayashibara Biochemical Laboratories, Inc.) was dissolved in distilled water to give a solution of a concentration of 10%. A certain amount of the solution and 5 ml of 500 mM phosphate buffer (pH 7.0) were put into measuring flask and filled up to 50 ml to give the test solutions containing AA-2G at the twofold concentration described in Table 1. Also the test solutions containing ascorbic acid were prepared in the same way except for using ascorbic acid (guaranteed regent) in place of AA-2G. Five ml of 500 mM phosphate buffer (pH 7.0) was filled up to 50 ml with distilled water to give control solution. Edible part of commercial mackerel fillet without bone and skin was chopped with trio blender and homogeneously stirred to make minced mackerel. Forty-five grams of the minced mackerel was put into a beaker and added with 45 g of the test solution or control solution to give the samples at the concentration of AA-2G or ascorbic acid described in Table 1. The samples were treated with homogenizer (produced by IKA Works Inc.) at ice-chilled temperature to give the homogenates as the test samples. PH of the homogenates is from 6.21 to 6.38.

Measurement of Hydrogen Sulfide Production

Ten grams of the above samples were put into 20 ml-vials and sealed with butyl rubber cap and aluminum seal. They were heated in boiled water bath for 15 minutes and cooled in running cool water. After cooled, they were heated on heating block (80° C.) for 10 minutes and the solidified samples were broken with vortex mixer. The amounts of hydrogen sulfide in the headspace gas were measured by hydrogen sulfide detecting tube (GASTEC No. 4LT, produced by GL Sciences Inc.). The amounts of produced hydrogen sulfide from 1 g of mackerel meat were shown in Table 1. Also the inhibiting rate (%) of hydrogen sulfide production were shown in Table 1, which were obtained by subtracting the percentage amounts of hydrogen sulfide produced from 1 g of mackerel meats added with test solutions relative to the amount of hydrogen sulfide produced from 1 g of mackerel meat added with control solution from 100 to obtain.

TABLE 1

| Test sample | | Produced | Inhibiting rate of volatile |
|---|---|---|---|
| Additive | Concentration in Sample (%) | Volatile sulfide (µg/g-mackerel) | sulfide production (%) |
| None | 0 | 43.2 | 0 |
| AA-2G | 0.0001 | 44.5 | −3.0 |
| | 0.0005 | 30.7 | 28.9 |
| | 0.001 | 17.4 | 59.7 |
| | 0.005 | 11.5 | 73.4 |
| | 0.01 | 13.2 | 69.4 |
| | 0.025 | 16.1 | 62.7 |
| | 0.05 | 19.9 | 53.9 |
| | 0.1 | 25.9 | 40.0 |
| | 0.5 | 38.2 | 11.6 |
| | 1.0 | 48.5 | −12.3 |
| Ascorbic acid | 0.0001 | 44.1 | −2.1 |
| | 0.0005 | 43.4 | −0.5 |
| | 0.001 | 43.6 | −0.9 |
| | 0.005 | 42.9 | 0.7 |
| | 0.01 | 71.7 | −66.0 |
| | 0.025 | 133.9 | −210.0 |
| | 0.05 | 139.3 | −222.5 |
| | 0.1 | 207.1 | −379.4 |
| | 0.5 | 257.4 | −495.8 |
| | 1.0 | 287.8 | −566.2 |

As is evident from Table 1, AA-2G inhibited the hydrogen sulfide production from homogenate of mackerel meat at the concentration in a range from 0.0005 to 0.5% unlike with control, however hydrogen sulfide production was enhanced at the AA-2G concentration of 0.1%. The inhibiting intensity became higher along with the decrease of AA-2G concentration. On the contrary, hydrogen sulfide production was enhanced when ascorbic acid was added at the concentration of 0.01% or more, whereas hydrogen sulfide production was equal to control when added at the concentration of 0.005% or less. These results indicate that AA-2G is useful as an efficient inhibitor of hydrogen sulfide production from a composition unlike with ascorbic acid when added to the composition at the concentration in a range from 0.0005 to 0.5% of the whole weight of the composition. The concentration is preferable to be 0.001% to 0.1%, more preferable to be 0.005% to 0.1%.

Experiment 2

Effect of AA-2G on Production of Dimethyl-Sulfide and Dimethyl-Disulfide

The experiments to investigate the effect of AA-2G on production of dimethyl-sulfide and dimethyl-disulfide were carried out as follows.

Preparation of Sample for Measurement of Production of Dimethyl-Sulfide and Dimethyl-Disulfide AA-2G (reagent grade, commercialized by Hayashibara Biochemical Laboratories, Inc.) was added in commercial milk to give the concentrations described in Table 2 to make the test solutions. Test solutions containing ascorbic acid were prepared in the same way except for using ascorbic acid (guaranteed regent) in place of AA-2G. The commercial milk was used plain as control. Sensory test of the solutions was performed by 11 panelists to evaluate the taste of each test solution added with AA-2G or ascorbic acid as being different (D) from control or as being the same (S) as control. The taste of each sample based on a same evaluation given by six or more of the 11 panelists was shown in Table 2. As a result, eight or more of the 11 panelists gave a same evaluation to each test solution.

Measurement of Production of Dimethyl-Sulfide and Dimethyl-Disulfide

One ml of the above samples were put into 20 ml-vials and sealed with butyl rubber cap and aluminum seal. After heated at 130° C. for one minute, the amounts of dimethyl-sulfide and dimethyl-disulfide in the headspace were measured by gas chromatography in conventional way. The amounts of dimethyl-sulfide and dimethyl-disulfide produced form 1 ml of samples were shown in Table 2. The sums of them were shown as the amounts of volatile sulfide in Table 2. Also the inhibiting rates (%) of volatile sulfide production were shown in Table 2, which were obtained by subtracting the percentage amounts of volatile sulfide produced from ml of the test solutions relative to the amount of volatile sulfide produced from 1 ml of control (milk) from 100 to obtain.

TABLE 2

| Test sample | | Produced | Produced | Produced | Inhibiting rate of volatile | |
|---|---|---|---|---|---|---|
| Additive | Concentration in Sample (%) | Dimethyl-sulfide (µg/ml-milk) | Dimethyl-disulfide (µg/ml-milk) | Volatile sulfide (µg/g-mackerel) | sulfide production (%) | Taste |
| None | 0 | 1.32 | 0.57 | 1.89 | 0 | S |
| AA-2G | 0.0001 | 1.30 | 0.54 | 1.94 | 2.6 | S |

TABLE 2-continued

| Test sample | | Produced Dimethyl-sulfide (μg/ml-milk) | Produced Dimethyl-disulfide (μg/ml-milk) | Produced Volatile sulfide (μg/g-mackerel) | Inhibiting rate of volatile sulfide production (%) | Taste |
|---|---|---|---|---|---|---|
| Additive | Concentration in Sample (%) | | | | | |
|  | 0.0005 | 1.12 | 0.43 | 1.55 | 18.0 | S |
|  | 0.001 | 0.75 | 0.37 | 1.12 | 40.7 | S |
|  | 0.005 | 0.23 | 0.14 | 0.37 | 80.4 | S |
|  | 0.01 | 0.11 | 0.14 | 0.25 | 86.8 | S |
|  | 0.05 | 0.07 | 0.07 | 0.14 | 92.6 | S |
|  | 0.1 | 0.06 | 0.07 | 0.13 | 93.1 | S |
|  | 0.5 | 0.10 | 0.08 | 0.18 | 90.5 | S |
|  | 2.5 | 0.28 | 0.19 | 0.47 | 75.1 | D |
| Ascorbic acid | 0.0001 | 1.32 | 0.56 | 1.88 | 0.5 | S |
|  | 0.0005 | 1.41 | 0.54 | 1.95 | −3.2 | S |
|  | 0.001 | 1.28 | 0.51 | 1.79 | 5.3 | S |
|  | 0.005 | 0.71 | 0.24 | 0.95 | 49.7 | S |
|  | 0.01 | 0.45 | 0.21 | 0.66 | 65.1 | S |
|  | 0.05 | 0.54 | 0.18 | 0.72 | 61.9 | S |
|  | 0.1 | 0.61 | 0.27 | 0.88 | 53.4 | S |
|  | 0.5 | 0.74 | 0.31 | 1.05 | 44.4 | S |
|  | 2.5 | 1.07 | 0.38 | 1.45 | 23.3 | D |

As is evident from Table 2, the production of volatile sulfides (dimethyl-sulfide and dimethyl-disulfide) from the test solutions was inhibited when AA-2G was added at the concentration of 0.0005% or more compared to control. When the AA-2G concentration in the milk was from 0.005 to 0.5%, volatile sulfides production was strongly inhibited. On the contrary, the inhibition intensity of volatile sulfides production was equal to control when ascorbic acid was added at the concentration of 0.001% or less. Although volatile sulfide production was inhibited when ascorbic acid was added at the concentration of 0.005%, the inhibition intensity was small compared to when AA-2G was added. The results of the sensory test indicate that addition of AA-2G or ascorbic acid at the concentration of 0.5% or less did not alter the taste of the milk whereas they alter the taste of the milk at the concentration of 2.5%. These results indicate that AA-2G is useful as a volatile sulfide production inhibitor as it can inhibit volatile sulfide production from a composition without altering the taste when added at the concentration from 0.0005 to 0.5%. The efficacy was larger than ascorbic acid. The concentration is preferable to be 0.005 to 0.5% to obtain sufficient efficacy.

The following examples further explain the present invention in detail. Needless to say, the present invention is not restricted to the examples.

EXAMPLE 1

Volatile Sulfide Production Inhibitor

Fifteen parts by weight of "ASCOFLESH", AA-2G commercialized by Hayashibara Shoji Inc., Okayama, Japan, four parts by weight of sodium carbonate, and 81 parts by weight of "TREHA", hydrous crystalline α,α-trehalose commercialized by Hayashibara Shoji Inc., Okayama, Japan, were mixed to homogeneity to make into a powdery volatile sulfide production inhibitor. The product can be advantageously used as an agent for inhibiting the production of volatile sulfides from compositions such as foods and beverages.

EXAMPLE 2

Volatile Sulfide Production Inhibitor

Ten parts by weight of "AA2G", AA-2G commercialized by Hayashibara Biochemical Laboratories Inc., Okayama, Japan, and five parts by weight of sodium carbonate were dissolved in 200 parts by weight of water. Successively, 120 parts by weight of "HALLODEX", a syrupy saccharide composition comprising saccharide-derivatives of α,α-trehalose (dry solid 72%) commercialized by Hayashibara Shoji Inc., Okayama, Japan, was dissolved in the above solution, and then the resulting solution was spray-dried by the conventional method to make into a powdery volatile sulfide production inhibitor. The product can be advantageously used as an agent for inhibiting the production of volatile sulfides from compositions such as foods and beverages.

EXAMPLE 3

Volatile Sulfide Production Inhibitor

Twenty parts by weight of "AA2G", AA-2G commercialized by Hayashibara Biochemical Laboratories Inc., Okayama, Japan, 70 parts by weight of cyclic tetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} produced by Hayashibara Biochemical Laboratories Inc., Okayama, Japan, and 10 parts by weight of "HAYASHIBARA GLUCOSYL-HESPERIDINE S", glucosyl-hesperidine commercialized by Hayashibara Shoji Inc., Okayama, Japan, were mixed to homogeneity to make into a powdery volatile sulfide production inhibitor. The product can be advantageously used as an agent for inhibiting the production of volatile sulfides from compositions such as foods and beverages.

EXAMPLE 4

Seasoned Extract of Dried Bonito Flake

Dried bonito flake was prepared in a usual manner of boiling a fresh bonito except for using an aqueous solution prepared by dissolving the powdery volatile sulfide production inhibitor, obtained by the method in Example 1 to give a concentration of 1% into water. Since the product comprises the volatile sulfide production inhibitor of the present invention, the production of volatile sulfides formed by the decomposition of proteins and sulfur amino acids was inhibited even after preserving at a room temperature for six months. Further, the production of volatile aldehydes and amines, formed by the oxidation and decomposition of lipids, was also inhibited. The product was not extremely dried and stably kept a good relish such as taste, flavor, color and texture derived from dried bonito flake for a long period.

After preserving the product at a room temperature for six months, the product was chipped by a grinder. One hundred parts of the resultant was admixed with 500 parts by weight of water, boiled for five minutes, and cooled to obtain an extract of dried bonito flake. The extract had satisfactory taste and flavor nearly equal to that obtained using freshly prepared dried bonito.

The extract was concentrated to ten-folds, and six parts by weight of the concentrate was admixed with four parts by weight of "TREHA", hydrous crystalline α,α-trehalose commercialized by Hayashibara Shoji Inc., Okayama, Japan, and 0.05 part by weight of the powdery volatile sulfide production inhibitor, obtained by the method in Example 2. Then, the resulting mixture was stirred for dissolving the additives and spray-dried by the conventional method to make into powdery soup stock. The production of volatile sulfides from the product is inhibited. Further, the production of volatile aldehydes and amines, formed by the oxidation and decomposition of lipids, is also inhibited. The product is a powdery soup stock having satisfactory taste and flavor of dried bonito flake. Since the product is so stable as to be free from casing and keep fluidity equal to that of a freshly prepared product, it can be preferably used alone or in combination with other extracts for producing a soup stock or seasoning in the form of powder, liquid, solid or paste.

EXAMPLE 5

Processed Sea Urchin Product

The powdery volatile sulfide production inhibitor, obtained by the method in Example 1, was diluted 1.000-folds with water and then sodium chloride and sodium lactate were dissolved in the solution to give concentrations of 0.8% and 0.1%, respectively, to make into a solution for soaking. A fresh ovary of sea urchin, placed in a basket, was soaked in the solution, kept at 5° C. for 10 hours, and dehydrated by taking up the basket to obtain a product. The product shows almost no production of volatile sulfides such as hydrogen sulfide and ethyl-mercaptan. Further, the production of volatile aldehydes and amines, both formed by the oxidation and decomposition of lipids in the product is inhibited. The product has a satisfactory taste, flavor, color and texture. When the product was tasted after preserved in a cooled-, chilled- or frozen-condition for six months, it was not denaturated, drips was not generated after thawing, and a granule form of sea urchin was not broken due to preservation in any above condition. When the product was cooked in a usual manner, it had a satisfactory taste, flavor, color and texture because the production of volatile sulfides and volatile aldehydes and amines, both formed by the oxidation and decomposition of lipids, in the product is inhibited.

EXAMPLE 6

Dried Blowfish

One hundred parts by weight of raw blowfish fillet rolled to about 8 mm in thickness was soaked in a solution, prepared by dissolving "ASCOFLESH", food grade AA-2G commercialized by Hayashibara Shoji Inc., Okayama, Japan, and "TREHA", α,α-trehalose commercialized by Hayashibara Shoji Inc., Okayama, Japan, into water to give concentrations of 0.005% and 3%, respectively. After soaking for 30 minutes and removing the solution, the blowfish fillet was dried overnight to obtain a product. The product is a dried blowfish retaining freshness because the production of volatile sulfides such as hydrogen sulfide and ethyl-mercaptan and volatile aldehydes and amines, formed by the oxidation and degradation of lipids, is inhibited. The product has a satisfactory taste, flavor, color and texture with almost no formation of amines such as trimethylamine as well as volatile sulfides even when it is broiled by the conventional method.

EXAMPLE 7

Minced and Steamed Fish Meat

To 2,000 parts by weight of fresh meat of Alaska pollock, pre-washed with water, one part by weight of AA-2G, 100 parts by weight of "HALLODEX", a saccaride composition comprising saccharide-derivatives of α,α-trehalose in a syrupy form, commercialized by Hayashibara Shoji Inc., Okayama, Japan, and three parts by weight of sodium lactate were added and the resulting mixture was minced and frozen at −20° C. to make into a frozen minced fish meat. After freezing at −20° C. for 90 days, the frozen minced fish meat was thawed. Separately, 40 parts by weight of sodium glutamate, 100 parts by weight of potato starch, three parts by weight of sodium polyphosphate, 50 parts by weight of sodium chloride, and five parts by weight of sorbitol were dissolved in 150 parts by weight of ice-cold water. One hundred parts by weight of the resulting solution was admixed with the above minced fish meat. The mixture was further minced and divided into about 120 grams each, and then each divided minced fish meat was shaped on a board. The resulting minced fish meat was steamed for 30 minutes to give an internal temperature of about 80° C. Successively, the product was cooled in an ambient temperature and stand at 4° C. for 24 hours to make into a minced and steamed fish meat. The frozen minced fish meat of Alaska pollock has satisfactory preservation stability because the production of volatile sulfides is inhibited by AA-2G and also the production of volatile aldehydes and volatile amines, formed by the oxidation and decomposition of lipids, is inhibited. The product keeps preferable relish such as taste, flavor, color, texture, etc. just after preparation even after preserving under a frozen condition and thawing.

EXAMPLE 8

Boiled Egg

Flesh eggs were placed in a pan and then an aqueous solution prepared by dissolving one part by weight of the powdery volatile sulfide production inhibitor, obtained in Example 1, into 999 parts by weight of water was poured into the pan to soak eggs. After boiling at 90° C. for 16 min, eggs were cooled with running water and removed the shell to make into boiled eggs. Successively, the boiled eggs were soaked in a seasoned solution prepared by dissolving 40 parts by weight of α,α-trehalose, 20 parts by weight of soy sauce, and two parts by weight of sodium chloride into 138 parts by weight of water. After soaking for two hours, the eggs were dehydrated, packed in a retort pouch and heated. The production of volatile sulfides such as hydrogen sulfide and ethyl-mercaptan from the product is inhibited. Also, the production of volatile aldehydes and amines, formed by the oxidation and decomposition of lipids, is inhibited. The product is delicious boiled eggs with satisfactory softness and can be preferably used as a material of "Oden" (Japanese hotchpotch).

EXAMPLE 9

Bacon

Twenty-two parts by weight of sodium chloride, 2.5 parts by weight of "TREHA", α,α-trehalose commercialized by Hayashibara Shoji Inc., Okayama, Japan, two parts by weight of sucrose, two parts by weight of sodium lactate, two parts by weight of sodium polyphosphate, 0.005 part by weight of "ASCOFLESH", AA-2G commercialized by Hayashibara Shoji Inc., Okayama, Japan, and 0.2 part by weight of sodium nitrite were admixed with 69.1 parts by weight of water and dissolved to make into a pickle-solution. To nine parts by weight of pork lib, one part by weight of the above pickle-solution was injected to penetrate the solution into the meat evenly. The resulting meat was smoked by the conventional method to make into bacon. After smoking, the bacon was leaved at an ambient temperature for overnight and then sliced, vacuum-sealed, and preserved at 10° C. The production of volatile sulfides; volatile aldehydes and volatile amines, both formed by the oxidation and decomposition of lipids, were inhibited; and the product keeps flavor just after preparation even after preserving for one week. The bacon shows good flavor after preserving with frozen condition and thawing.

EXAMPLE 10

Mayonnaise-Type Product

Ten parts by weight of vinegar, 7.5 parts by weight of powdery maltitol, eight parts by weight of sterilized whole egg, six parts by weight of water, two parts by weight of sodium chloride, 0.5 part by weight of sucrose, 0.5 part by weight of mustard powder, 0.5 part by weight of sodium glutamate, and 0.005 part by weight of "ASCOFLESH", AA-2G commercialized by Hayashibara Shoji Inc., Okayama, Japan, were mixed by stirring. Then, 45 parts by weight of salad oil was admixed with the mixture and emulsified by the conventional method to make into mayonnaise-type product. The product shows almost the same texture with mayonnaise. Since the production of volatile sulfides; volatile aldehydes and volatile amines, both formed by the oxidation and decomposition of lipids; and, further, the separation of lipids were inhibited by AA-2G and maltitol, the product stably keeps the quality when it is preserved for along period under ambient, chilled, refrigerated, or frozen conditions.

EXAMPLE 11

Milk

Milk was prepared by dissolving 0.01 part by weight of the powdery volatile sulfide production inhibitor, obtained by the method in Example 1, into 100 parts by weight of fresh milk. Since the production of volatile sulfides such as hydrogen sulfide from the product is inhibited, the product shows no bad smell when it is heated. The product keeps preferable taste and flavor of the milk and is advantageously used directly or as a material of milk beverages and lactic acid drinks.

EXAMPLE 12

Milk Custard

Five parts by weight of hard flour, nine parts by weight of sucrose, six parts by weight of "TREHA", hydrous crystalline α,α-trehalose commercialized by Hayashibara Shoji Inc., Okayama, Japan, three parts by weight of a saccharide composition comprising saccharide-derivatives of α,α-trehalose, and 0.05 part by weight of the powdery volatile sulfide production inhibitor, obtained by the method in Example 2, were mixed well, and then 63 parts by weight of fresh milk, 11 parts by weight of egg yolk, and three parts by weight of butter were further admixed with the mixture. Successively, the resulting mixture was heated to about 90° C. with stirring and made into custard cream by the conventional method. Since the product comprises α,α-trehalose and a saccharide composition comprising saccharide-derivatives of α,α-trehalose together with AA-2G, the production of volatile sulfides such as hydrogen sulfide, dimethyl-sulfide and dimethyl-disulfide by heating is inhibited, the product shows no bad smell and keeps its appearance and flavors just after preparation even after preserving it in a freezer. Also, the bakery products, prepared by using the product, such as baked confectionary has a good flavor because the production of volatile sulfides from the custard during the baking process is inhibited.

EXAMPLE 13

Polished Rice

An aqueous solution containing 20% of α,α-trehalose and 0.0025% of "ASCOFLESH", AA-2G commercialized by Hayashibara Shoji Inc., Okayama, Japan, was prepared. Then, four parts by weight of the resulting solution was sprayed equally on 100 parts by weight of unpolished rice (old rice) with stirring. After standing the resulting unpolished rice for overnight, the unpolished rice was polished by the conventional method using a polishing machine to make into polished rice. The product is a high quality polished rice with good preservation stability because the production of volatile sulfides, volatile amines, and volatile aldehydes from the product is inhibited. The product can be advantageously used as a material of cooked rice, rice ball, rice gruel, etc. with a good flavor. The product can be advantageously used intact as pre-washed rice and after processing into gelatinized rice. Rice bran, obtained as a by-product by the above polishing process, also comprises AA-2G, which are effective ingredients of the present invention, and α,α-trehalose. Therefore, the production of volatile sulfides and volatile aldehydes and amines, both formed by the oxidation and decomposition of lipids from the rice bran is inhibited and the rice bran has a satisfactory preserving stability. The rice bran can be advantageously used for producing rice bran pickles and as a material of rice bran oil. Further, the rice bran can be advantageously used intact or in the defatted form as a material of mixed feeds.

EXAMPLE 14

Chocolate Cookie

Chocolate cookie was prepared by the conventional method using 140 parts by weight of soft flour, 90 parts by weight of butter, 115 parts by weight of chocolate, 360 parts by weight of sucrose, 200 parts by weight of whole egg, 200 parts by weight of almond, and 0.1 part by weight of the powdery volatile sulfide production inhibitor, prepared by the method in Example 3. The production of volatile sulfides from the product is inhibited even after preserving for three months at an ambient temperature. Further, since the production of volatile aldehydes and amines, formed by the oxidation and decomposition of lipids, and volatile substances such as diones from chocolate are inhibited, the product keeps flavor of just after preparation.

EXAMPLE 15

Powdery Peptide Product

One part by weight of "HINUTE-S", 20% soybean peptide solution commercialized by Fuji Oil Co., Ltd., Osaka, Japan, three parts by weight of α,α-trehalose, and 0.0005 part by weight of the powdery volatile sulfide production inhibitor prepared in Example 3 were mixed, dried at 50° C. in reduced pressure, and pulverized to make into a powdery peptide product. The production of volatile sulfides from the product is inhibited even when the product is preserved for a long period. The product can be advantageously used as a material of foods and beverages such as isotonic drink, health foods and baby food, and nutritional supplement for treating as well as a material for confectionaries such as premix and frozen dessert.

EXAMPLE 16

| Ointment for curing wound | |
|---|---|
| (Formula A) | |
| Macrogol (400) | 450 parts by weight |
| Carboxyvinyl polymer | 3 parts by weight |
| Castor oil | 1 part by weight |
| Isopropanol | 400 parts by weight |
| Chlorhexidine gluconate solution | 1 part by weight |
| (Formula B) | |
| Saccharide composition comprising saccharide-derivatives of α,α-trehalose in a syrupy form ("TORNARE" commercialized by Hayashibara Biochemical Laboratories Inc., Okayama, Japan | 70 parts by weight |
| Sodium hydroxide | 3 parts by weight |
| Pullulan | 1 part by weight |
| AA-2G ("AA2G", commercialized by Hayashibara Biochemical Laboratories Inc., Okayama, Japan | 0.001 part by weight |
| Collagen | 3 parts by weight |
| Purified water | 73 parts by weight |

According to the above formulae, ingredients in Formula A were mixed during stirring in vacuo by a conventional method. Successively, ingredients in Formula B were mixed to the above mixture to make into an ointment for curing wound, which exhibits adequate extendability and adhesiveness. The production of volatile sulfides and aldehydes from the product is inhibited. Since the product shows no stickyness after using it and exhibits a satisfactory sense of use, it can be used for curing wounds such as incised wound, scratch, burn injury, athlete's foot, chilblain, and pressure sore by applying it to wound directly or with using gauzes.

EXAMPLE 17

| Cosmetic cream | |
|---|---|
| (Formula A) | |
| Polyoxyethyleneglycol monostearate | 2 parts by weight |
| Self-emulsifying glycerin monostearate | 5 parts by weight |
| Potassium DL-lactate | 5 parts by weight |
| Behenylalcohol | 1 part by weight |
| Eicosatetraenoic acid | 2 parts by weight |
| Liquid paraffin | 1 part by weight |
| Glycerin trioctanoate | 10 parts by weight |
| Preservative | suitable amount |
| (Formula B) | |
| Cyclic tetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} (produced by Hayashibara Biochemical Laboratories Inc.) | 7 parts by weight |
| 1,3-Butyleneglycol | 3 parts by weight |
| Taurine | 1 part by weight |
| Collagen | 1 part by weight |
| AA-2G ("AA2G", Commercialized by Hayashibara Biochemical Laboratories Inc., Okayama, Japan | 0.005 part by weight |
| Purified water | 64 parts by weight |

According to Formula A, ingredients described above were mixed and dissolved by heating by a conventional method. After mixing ingredients in Formula B to the above mixture, the resulting mixture was emulsified using a homogenizer, admixed with suitable amount of fragrance and further mixed with stirring to make into a cosmetic cream. Since the production of volatile aldehydes and volatile amines as well as volatile sulfides from the product is inhibited, the product is a whitening cream having a high quality and safety with no deterioration of colors and no bad smell. The product can be advantageously used for preventing cutaneous stimulation and itch, further, for treating and/or preventing the deposition of pigment such as fleck, freckles, and sunburn. The product exhibits a satisfactory sense of use and shows no stickyness when applied it on the skin.

INDUSTRIAL APPLICABILITY

As described above, the present invention relates to a volatile sulfide production inhibitor comprising AA-2G as an effective ingredient and a method for inhibiting the production of volatile sulfides from a composition characterized in that said inhibitor is incorporated into said composition. AA-2G is a safe substance exerting the function of vitamin C in the living body when it is ingested through oral or parenteral pathway. Accordingly, the volatile sulfide production inhibitor and the method for inhibiting the production of volatile sulfides using the inhibitor of the present invention can be used in various fields such as foods and beverages, cosmetics, quasi drugs, pharmaceuticals, feedstuffs, baits, and pet foods. The present invention, having these outstanding functions and effects, is a significantly important invention that greatly contributes to this art.

The invention claimed is:

1. A method for inhibiting the production of volatile sulfides, comprising
incorporating, as a volatile sulfide production inhibitor, α-D-glucopyranosyl-(1→2)-L-ascorbic acid, substantially free of an effective amount of any other foul odor inhibitor, into a composition,
which composition comprises (1) sulfur amino acids or (2) peptides containing sulfur amino acids, and which produces said volatile sulfides by heating or longtime storage,
wherein said volatile sulfides are selected from the group consisting of hydrogen sulfide, methyl-mercaptan, dimethyl-sulfide, and dimethyl-disulfide,
wherein said α-D-glucopyranosyl-(1→2)-L-ascorbic acid is incorporated into said composition in an amount of 0.001 to 0.1% (w/w) of the total weight of said composition and inhibits the production of said volatile sulfide without deteriorating the original flavor of said composition.

2. The method of claim 1, wherein one or more members selected from the group consisting of maltitol, and cyclic tetrasaccharide is incorporated into said composition together with said α-D-glucopyranosyl-(1→2)-L-ascorbic acid.

* * * * *